(12) United States Patent
Seo et al.

(10) Patent No.: US 8,071,093 B1
(45) Date of Patent: Dec. 6, 2011

(54) FULLY HUMAN ANTI-EPIDERMAL GROWTH FACTOR RECEPTOR ANTIBODIES

(75) Inventors: Sang Won Seo, Hwaseong-si (KR); A Yeon Cho, Seoul (KR); Sung Young Jeong, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/781,236

(22) Filed: May 17, 2010

(51) Int. Cl.
*A61K 39/395* (2006.01)
*A61K 39/00* (2006.01)
*G01N 33/53* (2006.01)
*G01N 33/563* (2006.01)
*G01N 33/574* (2006.01)
*C07K 16/28* (2006.01)
*C12P 21/08* (2006.01)

(52) U.S. Cl. ............... 424/130.1; 424/141.1; 424/142.1; 424/143.1; 424/178.1; 424/183.1; 435/7.1; 435/7.2; 435/7.3; 530/387.1; 530/388.1; 530/388.15; 530/388.22; 530/391.3; 530/391.7

(58) Field of Classification Search ............... None
See application file for complete search history.

(56) References Cited

U.S. PATENT DOCUMENTS 5,558,864 A * 9/1996 Bendig et al. ............ 424/133.1
2009/0286283 A1 * 11/2009 Lee et al. .................... 435/69.7

OTHER PUBLICATIONS

Wu et al, J. Mol. Biol. 294: 151-162, 1999.*
Rudikoff et al, Proc Natl Acad Sci USA 79: 1979-1983, 1982.*
Henry et al, Cancer Res. 64: 7995-8001, Nov. 1, 2004.*
Stancovski et al, Proceedings of the National Academy of Science USA 88: 8691-8695, 1991.*
Riemer et al, Mol. Immunol. 42: 1121-1124, 2005.*
Cochran et al, J. Immunol. Meth. 287: 147-158, 2004.*
Goldstein, N.I. et al., Biological Efficacy of a Chimeric Antibody to the Epidermal Growth Factor Receptor in a Human Tumor Xenograft Model, Clin Cancer Res. 1995; 1(11): 1311-1318.
Vaughan, T.J. et al., Human Antibodies with Sub-nanomolar Affinities Isolated from a Large Non-immunized Phage Display Library, Nature Biotechnology 1996;14: 309-314.

* cited by examiner

*Primary Examiner* — Phuong Huynh
(74) *Attorney, Agent, or Firm* — Cantor Colburn LLP (57) ABSTRACT

Disclosed are fully human anti-epidermal growth factor receptor (EGFR) antibodies, fragments thereof, and nucleic acid sequences encoding for the same. Further disclosed are methods of making and using the antibodies.

8 Claims, 4 Drawing Sheets

FULLY HUMAN ANTI-EPIDERMAL GROWTH FACTOR RECEPTOR ANTIBODIES

BACKGROUND

1. Field

Disclosed are fully human anti-epidermal growth factor receptor (EGFR) antibodies, fragments thereof and applications thereof.

2. Description of the Related Art

The development of antibodies has evolved from mouse antibodies, to chimeric antibodies, to humanized antibodies, and to fully human antibodies. Fully human antibodies are advantageous over other types of antibodies in that immune response in humans can be reduced. Thus, recent research is centered on the development of fully human antibodies.

Epidermal growth factor receptor (EGFR; alternatively called Erbb1 or HER1) is a 170-kDa, type 1 transmembrane molecule. Its expression is enhanced in many human tumors, including those in head, neck, breast, colon, prostate gland, lung and ovary. The overexpression of EGFR is known to be related with poor clinical prognosis. Further, expression of EGFR is often accompanied by the production of EGFR ligands, particularly tumor growth factor-α (TGF-α) and epidermal growth factor (EGF), by EGFR-expressing tumor cells. This autocrine loop is conjectured to be related to tumorigenesis. Accordingly, growth and survival of tumors can be suppressed by interrupting the interaction between EGFR ligands and EGFR.

SUMMARY

Disclosed herein are fully human anti-epidermal growth factor receptor (EGFR) antibodies and fragments thereof having antigen-binding capacity. Methods of making and using the antibodies and fragments thereof are also disclosed. The antibody or fragment thereof can be used in the diagnosis or treatment of an EGFR-related disease, e.g., cancer. In an embodiment, an isolated human monoclonal antibody that binds human epidermal growth factor receptor (EGFR) includes a heavy chain variable domain including a heavy chain complementarity determining region (H-CDR) 1 (H-CDR1) sequence of SEQ ID NO: 1, a conservative modification of SEQ ID NO:1, or an amino sequence that is at least 80% homologous with SEQ ID NO:1; an H-CDR2 sequence of SEQ ID NO: 2, a conservative modification of SEQ ID NO:2, or an amino sequence that is at least 80% homologous with SEQ ID NO:2; and an H-CDR3 sequence of SEQ ID NO: 3, a conservative modification of SEQ ID NO:3, or an amino sequence that is at least 80% homologous with SEQ ID NO:3; or a fragment of the antibody, wherein the fragment has EGFR-specific binding activity.

In an embodiment, the antibody includes a light chain variable domain including a light chain complementarity determining region (L-CDR) 1 (L-CDR1) sequence of SEQ ID NO: 4, a conservative modification of SEQ ID NO:4, or an amino sequence that is at least 80% homologous with SEQ ID NO:4; an L-CDR2 sequence of SEQ ID NO: 5, a conservative modification of SEQ ID NO:5, or an amino sequence that is at least 80% homologous with SEQ ID NO:5; and an L-CDR3 sequence of SEQ ID NO: 6, a conservative modification of SEQ ID NO:6, or an amino sequence that is at least 80% homologous with SEQ ID NO:6; or a fragment of the antibody, wherein the fragment has EGFR-specific binding activity.

In an embodiment, the antibody includes a heavy chain encoded by a polynucleotide consisting of nucleotides 1-1401 of SEQ ID NO: 7; and a light chain encoded by a polynucleotide consisting of SEQ ID NO: 8, or a fragment of the antibody, wherein the fragment has EGFR-specific binding activity.

Recombinant vectors, host cells, and methods of producing the antibody are disclosed herein A composition disclosed herein may include an antibody and a pharmaceutically acceptable carrier. Methods of using the antibody in treatment of EGFR-related diseases or in detection of EGFR are also disclosed.

BRIEF DESCRIPTION OF THE DRAWINGS

Description will be made in detail with reference to certain example embodiments which are illustrated in the accompanying drawings given hereinbelow by way of illustration only and thus are not limitative, wherein.

DETAILED DESCRIPTION

Human anti-epidermal growth factor receptor (EGFR)-antibodies are disclosed herein.

EGFR-expressing tumor cells that can be targeted (e.g., opsonified) by the human antibodies disclosed herein include tumor cells in bladder, breast, colon, kidney, renal cells, ovary, prostate gland, squamous cell, lung (non-small cells), head and neck. Other EGFR-expressing cells include synovial fibroblasts and keratinocytes, which may be target cells in the treatment of arthritis and psoriasis.

In another aspect, the human antibodies disclosed herein can inhibit cell signaling mediated by EGFR. For instance, the antibody can inhibit autophosphorylation of EGFR induced by binding an EGFR ligand (e.g., EGF or TGF-α). Further, the antibody may inhibit cell activation induced by the autocrines EGF or TGF-α, or may induce antibody-dependent cell-mediated cytotoxicity (ADCC) of EGFR-expressing cells in the presence of human polymorphonuclear cells. Examples of EGFR-expressing cells include, particularly, bladder cells, breast cells, colon cells, kidney cells, ovarian cells, prostate cells, renal cells, squamous cells, non-small lung cells, synovial fibroblasts, and keratinocytes.

The term "complementarity determining region (CDR)" used herein refers to relatively short amino acid sequences found in the heavy chain and light chain variable domains of antibodies that determine the specificity of the antibody and make contact with the specific antigen.

The term "antigen-binding activity" or "antigen-binding capacity" used herein refers to an activity or capacity to bind to an antigen possessed by a full-length antibody, a fragment of an antibody, a heavy chain variable domain, a light chain variable domain, or a CDR.

The term "specific" used herein refers to the ability of a sequence or an antibody to distinguish a specific antigen from one or more other reference antigens. This property is not absolute in nature, but relative.

With respect to an antibody, the term "fragment thereof having an antigen-binding activity" used herein refers to a fragment of the antibody having antigen-binding capacity, and may include Fab, F(ab'), F(ab')2, Fv, etc. Such fragments may be produced by recombinant techniques or enzymatic cleavage. For example, Fab or F(ab')2 fragment may be produced from an intact antibody by digesting with papain or pepsin, respectively. Fab is composed of the variable domains of the light and the heavy chains, a constant domain of the light chain, and a first constant domain (CH1) of the light chain. It has one antigen-binding site. F(ab') is different from Fab in that it has a hinge region having at least one cysteine residue at the C-terminal of the heavy chain CH1 domain. F(ab')2 has a structure in which the cysteine residues of the hinge region of Fab' form a disulfide bonding. Fv is the smallest fragment of the antibody having only the heavy chain variable domain and the light chain variable domain.

The term "homology" used herein refers to the percentage of identical residues between two sequences. For example, for two peptide sequences, homology refers to a percentage of identical amino acids between the two sequences. The homology may be at least 80%. Further, it may be at least 90%. Optionally, it may be at least 95%.

The term "linked" used herein refers to a linkage of two entities, for example a labeling material and an antibody, by covalent or non-covalent bonding. A linkage mediated by a linker molecule or the like is also included.

The term "toxic material" used herein refers to a material which can be linked to an antibody or a fragment thereof and can exert toxic effects on a target, such as a cancer cell. For example, radioactive materials such as yttrium-90, iodine-131, etc. and cytotoxic materials such as calicheamicin are included among toxic materials.

The term "labeling material" used herein refers to a material which binds to an antibody or a fragment thereof and is detectable by a physical or chemical method to permit identification of the location or quantity of the antibody or the fragment thereof. The labeling material is used to label the antibody to make detection of bound or unbound antibody easy. Suitable detectable materials include a variety of enzymes, prosthetic groups, fluorescent materials, light-emitting materials and radioactive materials. Examples of suitable enzymes include horseradish peroxidase, alkaline phosphatase, β-galactosidase or acetylcholinesterase. Examples of suitable prosthetic groups include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. Examples of light-emitting materials include luminol, and examples of radioactive materials include $^{125}$I, $^{131}$I, $^{35}$S, and $^{3}$H. Detection of the labeling material can be performed by any appropriate method known in the art.

The term "variant" refers to a protein or nucleic acid sequence in which at least one residue has been changed from the parent sequence.

For example, with respect to peptides, the term "variant" refers to a peptide in which at least one amino acid has been changed from the sequence of the parent peptide. Those skilled in the art will appreciate that any variant that has been determined to bind specifically to EGFR and to function as an antibody is encompassed within the scope of variants described herein. The variant may be produced by changing one or more amino acid residue of each CDR region, for example, by trinucleotide mutagenesis or any other method known in the art.

Variants include polypeptide variants in which the overall molecular structure of the peptide sequence is conserved. Given the information on the characteristics of each amino acid, those skilled in the art will appreciate some reasonable substitutions, e.g., conservative modifications. Such conservative substitutions may be carried out based on, for example, polarity, charge, solubility, hydrophobicity, hydrophilicity and/or amphiphilicity of corresponding residues. For example, amino acids may be classified into nonpolar (hydrophobic) amino acids, polar but neutral amino acids, positively charged (basic) amino acids, and negatively charged (acidic) amino acids. Nonpolar (hydrophobic) amino acids include alanine, leucine, isoleucine, valine, proline, phenylalanine, tryptophan and methionine. Polar but neutral amino acids include glycine, serine, threonine, cysteine, tyrosine, asparagine and glutamine. Positively charged (basic) amino acids include arginine, lysine and histidine. And, negatively charged (acidic) amino acids include aspartic acid and glutamic acid. Substitution may be possible within each group. Some possible substitutions may be made (i) between serine (S) and threonine (T); (ii) between proline (P) and glycine (G); and (iii) among alanine (A), valine (V), leucine (L) and isoleucine (I). Those skilled in the art may easily construct the DNAs encoding for the conservative amino acid variants through DNA recombination and synthesis techniques.

With respect to nucleic acids, variants of the nucleic acid molecules encoding for the polypeptides disclosed herein are also included. A "variant" of a nucleic acid can have 80% or more of nucleic acid sequence homology. Further, it can have 90% or more, or 95% or more sequence homology. Of the variants having the homology, those that can be hybridized even under very stringent condition are included.

The term "vector" used herein refers to a nucleic acid sequence to express a target gene in a host cell and includes a plasmid vector, a cosmid vector, a bacteriophage vector, a viral vector, etc. For example, the vector may be an expression vector including a membrane targeting or secretion signaling sequence or a leader sequence, in addition to an expression control element such as promoter, operator, initiation codon, termination codon, polyadenylation signal, and enhancer. The vector may be manufactured in various ways known in the art depending on the purpose. An expression vector may include a selection marker for selecting a host cell containing the vector. Further, a replicable expression vector may include an origin of replication.

The term "recombinant vector" used herein refers to a vector operably linked to a heterologous nucleotide sequence for the purpose of expression, production and isolation of the heterologous nucleotide sequence. The heterologous nucleotide sequence can be a nucleotide sequence encoding all or part of the heavy chain or the light chain of an antibody disclosed herein.

A single vector can be used to simultaneously express both the heavy chain and the light chain of the antibody. Alternatively, the heavy chain and the light chain of the antibody can be expressed from two different vectors. In the latter case, the two vectors may be introduced into a single host cell by simultaneous transduction or targeted transduction.

The host cell of the vector may be any cell that can be practically utilized by the expression vector. For example, the host cell may be a higher eukaryotic cell, such as a mammalian cell, or a lower eukaryotic cell, such as a yeast cell.

Further, the host cell may be a prokaryotic cell, such as a bacterial cell.

Examples of the CDR sequences of the heavy chain of EGFR-specific antibodies disclosed herein are given in the following Table 1.

TABLE 1

| | Heavy chain amino acid sequence | | |
|---|---|---|---|
| Clone name | CDR 1 | CDR 2 | CDR3 |
| Erbb1 78 | DYGMS (SEQ ID NO: 1) | GINWNGGSTGYADSVKG (SEQ ID NO: 2) | DYWGSLDY (SEQ ID NO: 3) |

Examples of the CDR sequences of the light chain of EGFR-specific antibodies disclosed herein are given in the following Table 2.

TABLE 2

| | Light chain amino acid sequence | | |
|---|---|---|---|
| Clone name | CDR 1 | CDR 2 | CDR3 |
| Erbb1 78 | TGTSSDVGGYNYVS (SEQ ID NO: 4) | DVNRRPS (SEQ ID NO: 5) | SSYVSTNTYV (SEQ ID NO: 6) |

A composition comprising the antibody, or a fragment thereof, disclosed herein as an effective ingredient and a pharmaceutically acceptable carrier is provided. The composition can be prepared according to any method known in the art. Examples of suitable pharmaceutically acceptable carriers and formulations are delineated, for example, in "Remington's Pharmaceutical Sciences" (18th ed., Alfonso R. Gennaro, Ed., Easton, Pa.: Mack Pub. Co., 1990). In order to prepare the composition, the antibody or the fragment thereof may be used in an amount effective for treatment along with a carrier. Formulations may be in a form suitable for controlled release of the active ingredient. Controlled-release formulations can be prepared by forming a complex using the antibody or the fragment thereof or using a polymer for absorbing the antibody or the fragment thereof. For example, polymers such as polyester, polyamino acid, polyvinylpyrrolidone, ethylene-vinyl acetate, methylcellulose, carboxymethylcellulose, or protamine can be used to control the release of the antibody or fragment thereof from the composition.

The composition may be administered parentally by injection, for example, bolus injection or continuous infusion. For this purpose, formulations can be made for parenteral administration. Formulations for injection may be provided in a unit administration form, e.g., in an ampule, or in multiple-administration containers, along with a preservative. The composition can be in the form of suspension, solution or emulsion of oil-based or water-based vehicles, and can include a formulation agent such as suspension agent, stabilizer or dispersant.

The composition may be provided in a dispenser unit or pack containing one or more unit administration forms of the effective ingredient. The pack can be made of, for example, metal or plastic foil.

The composition may be administered to a subject through any standard administration technique including oral, intravenous, intra-abdominal, subcutaneous, pulmonary, transdermal, intramuscular, intranasal, buccal, sublingual or suppository administration.

The dose of the composition may vary depending on the physical condition, age, sex and body weight of the patient, severity of disease, purpose of administration, and the like. A typical dose can be, for example, from 0.001 to 1000 μg/kg body weight. However, the dose may be lower or higher, considering the factors for a particular patient. A daily dose for parenteral administration may be from about 0.1 μg to about 100 mg/kg body weight, from about 0.3 μg to about 10 mg/kg body weight, from about 0.1 μg to about 1 mg/kg body weight, or from about 0.05 μg to about 1 mg/kg body weight.

Methods of using the antibodies disclosed herein are also provided. The antibody, or a fragment thereof having antigen-binding capacity, can be used to detect EGFR in a sample. In an embodiment, the method comprises contacting the antibody or fragment thereof with a sample under conditions such that the antibody binds EGFR; and detecting antibody bound to EGFR. Such a method could be a component of a diagnostic method for EGFR-expressing or overexpressing cells.

The antibody, or a fragment thereof, can also be used in methods of treating EGFR-related diseases, e.g. cancer or an autoimmune disease such as psoriasis. In an embodiment, the method comprises administering the antibody or fragment thereof to subject having the EGFR-related disease.

EXAMPLES

Hereinafter, description will be made in more detail through examples. However, the following examples are not intended to be limiting.

1. Phage Display Libraries

Phage display libraries (Korea Research Institute of Bioscience and Biotechnology, Daejeon, Korea) are used that express on the phage surface over 100 billion variable domains of the heavy chain and light chain of fully human antibodies derived from human blood and bone marrow in the form of single chain variable fragment (scFv).

2. Antigens

One antigen used is Erbb1-Fc (Korea Research Institute of Bioscience and Biotechnology, Daejeon, Korea), a protein construct in which the first 360 amino acids of human epithelial growth factor receptor (EGFR; NCBI Accession Number: P00533) including the first ligand binding domain and a furin-like repeat are linked with an Fc domain. The Erbb1-Fc is expressed in HEK-293 cells (ATCC, CRL-1573) and purified for use as an antigen. Commercially available human epithelial growth factor receptor (EGFR_human, Sigma, E3641) is used as another antigen.

3. Biopanning

Panning is carried out using an immunotube according to "Human antibodies with sub-nanomolar affinities isolated from a large non-immunized phage display library." *Nat Biotechnol;* 14(3):309-14, 1996, the entire contents of which are incorporated herein by reference. Specifically, 2 mL of coating buffer (0.1 M sodium carbonate buffer) is mixed with Erbb1-Fc (30 ug/mL) or EGFR_human (10 ug/mL) in an immunotube (Nunc). The antigen is fixed by revolving at 4° C. for 18 hours.

Figure 1:
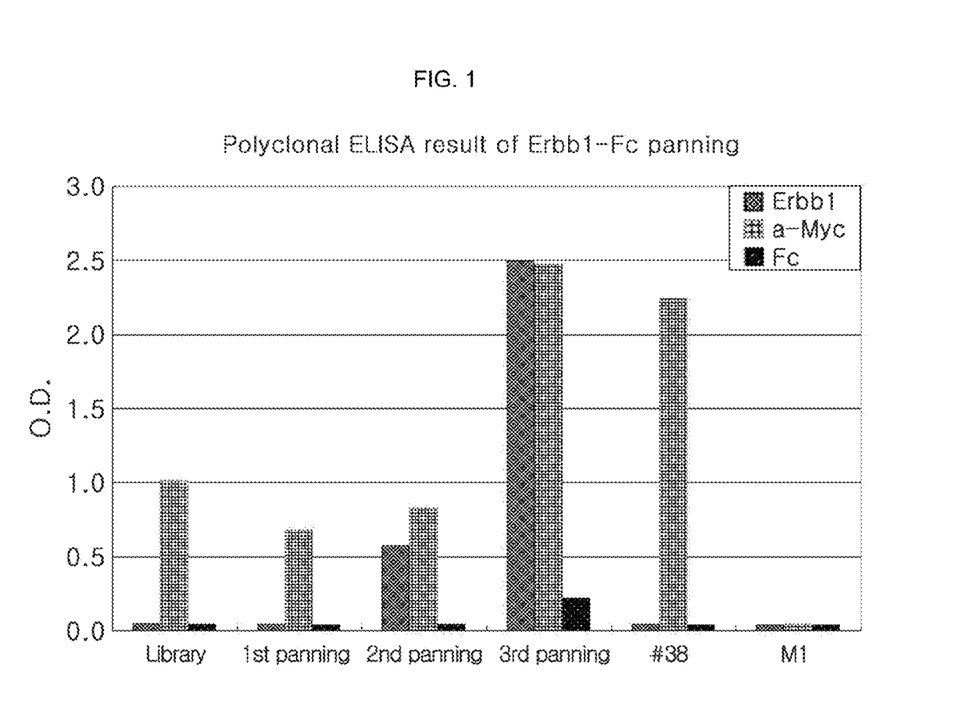
FIG. 1 is a graph showing the results of panning onto an Erbb1-Fc antigen-coated immunotube measured by enzyme-linked immunosorbent assay (ELISA)
Figure 2:
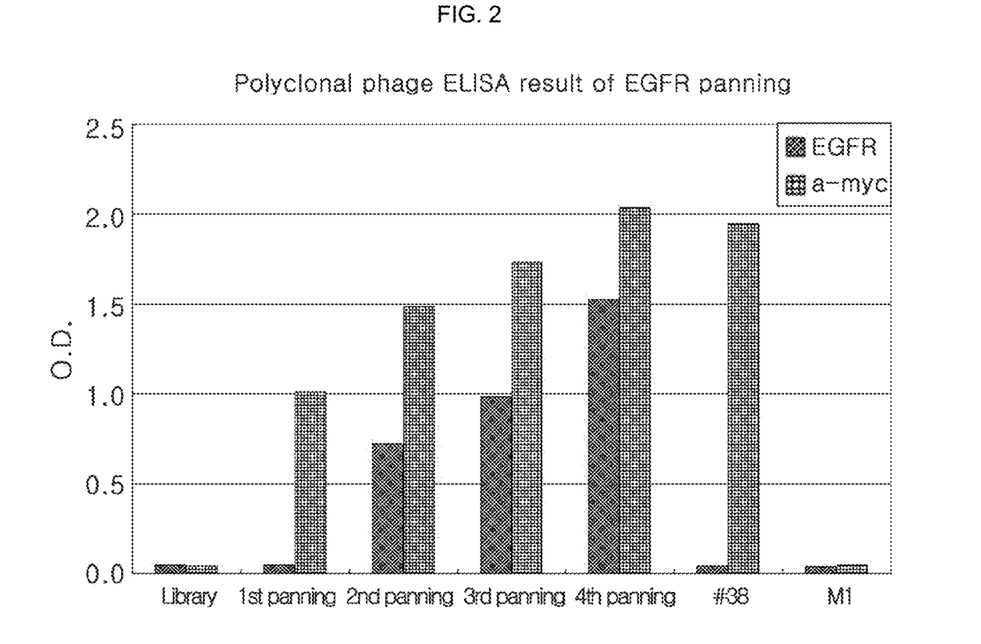
FIG. 2 is a graph showing the results of panning onto an EGFR_human antigen-coated immunotube measured by ELISA.

The antigen-fixed immunotube is blocked with 4% skimmed milk at room temperature for 2 hours and a previously prepared phage solution in which the antibody library is expressed is added. After 2 hours of incubation with revolution, followed by washing with PBS (phosphate buffered saline) and PBST (PBS+Tween 20), antigen-bound phages are separated. This panning procedure is repeated 3 or 4 times depending on the polyclonal phage enzyme-linked immunosorbent assay (ELISA) results. The results for Erbb1-FC as antigen are illustrated in FIG. 1 and for EGFR_human as antigen in FIG. 2. As seen in FIG. 1 and FIG. 2, the signal of the phages bound to Erbb1-Fc or EGFR_human increases gradually with the number of rounds of panning. Since the phage solution obtained from panning with Erbb1-Fc does not show a high Fc-bound phage signal, it is thought that the increasing phage signal is Erbb1 specific. Further, negative controls show that phage clones obtained from panning with a non-EGFR antigen (#38) or with the M1 helper phage (M1) do not bind to Erbb1 or EGFR_human.

4. Determination of Monoclonal Sequences

About 400 single phage clones are obtained from the 3rd or 4th round of panning. DNA is obtained from the 400 single phage clones and the scFv gene sequence is specifically amplified by polymerase chain reaction (PCR). The PCR product obtained is cleaved using BstNI restriction enzyme (New England Biolab; NEB) at 37° C. for 2 hours. The product is subjected to electrophoresis using 8% acrylamide gel, and only clones exhibiting specific patterns, different from the cleavage pattern of most other clones shown after running the electrophoresis, are subjected to DNA sequencing. DNA sequences obtained for one clone provide the CDR protein sequences for the heavy and light chain variable domains given in Tables 1 and 2.

5. Expression of Antibodies

The heavy chain and light chain variable domains obtained in 4 are cloned into different vectors. The heavy chain variable domain is cloned into a vector having a CMV (cytomegalovirus) promoter and also including the heavy chain constant domain. The light chain variable domain is cloned into a vector having a CMV promoter and including the light chain constant domain.

Specifically, the heavy chain variable domain and its vector are treated with the restriction enzymes SfiI (NEB) and NheI (NEB), and the light chain variable domain and its vector are treated with the restriction enzymes SfiI (NEB) and BglII (NEB). Subsequently, T4 DNA ligase (NEB) is used to ligate the heavy chain variable domain and the light chain variable domain into their respective vector for expressing the fully human antibody. The heavy chain vector and light chain vector are cotransfected into HEK-293E cells (Korea Research Institute of Bioscience and Biotechnology, Daejeon, Korea). The cells are cultured in serum-free Dulbecco's modified essential medium (DMEM, Invitrogen) while replacing the medium once every 3 days, for a total of 4 times. The culture medium contains fully human antibodies (IgG) with heavy and light chains, for example the IgG may contain the variable domain CDR sequences shown in Tables 1 and 2. The medium containing the expressed IgG is centrifuged to remove remaining cell fragments and impurities, and then the antibody is purified by affinity chromatography using protein A. Among the antibodies purified, the Erbb1 78 clone antibody has a heavy chain encoded by the polynucleotide of SEQ ID NO: 7 and a light chain encoded by the polynucleotide of SEQ ID NO: 8.

6. Measurement of Binding Capacity of scFv Clones Obtained from Panning

Figure 3:
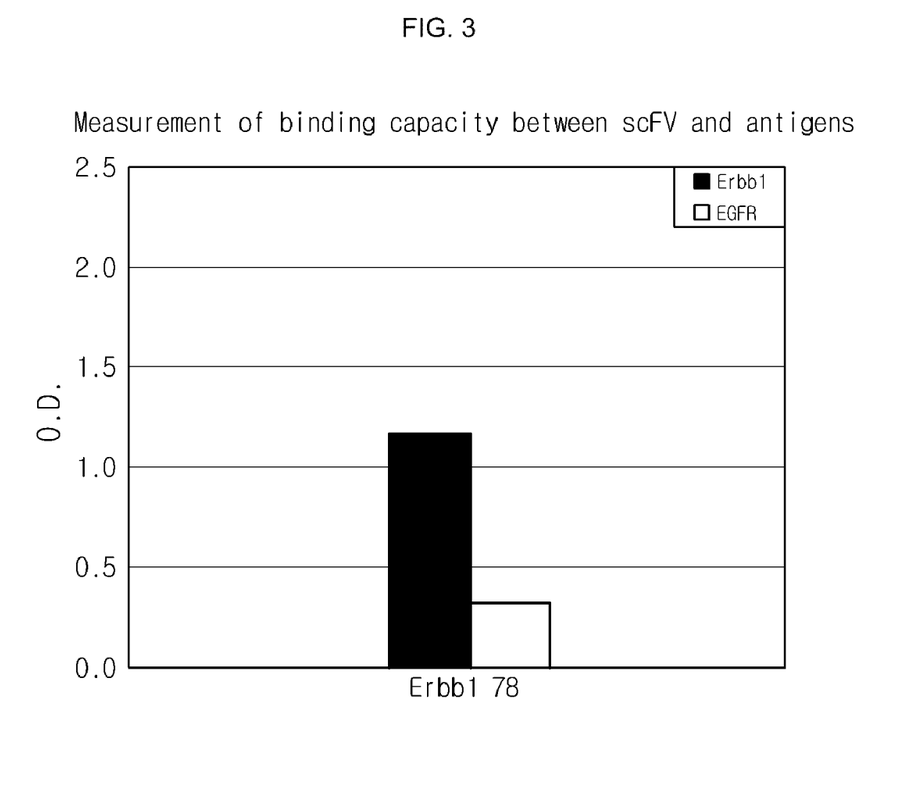
FIG. 3 is a graph showing the results of measuring binding capacity between a clone (Erbb1-78) obtained by panning and the antigens Erbb1-Fc and EGFR_human measured by ELISA.

Relative binding capacity between the scFv clones obtained from panning using Erbb1-Fc as antigen and the antigens Erbb1-Fc and EGFR_human (Sigma, E3641) is determined by ELISA. Antigens are fixed on a 96-well Maxisorp plate (Nunc) and phages obtained from panning, including the Erbb1 78 clone, are added individually to wells to determine binding. After 2 hours of binding reaction at 37° C., the plate is washed with 0.05% PBST. Then, after 30 minutes of reaction with HRP (horseradish peroxidase)-bound anti-M13 antibody (GE Healthcare), staining is carried out using OPD (o-phenylenediamine dihydrochloride) substrate (Sigma). The result is illustrated in FIG. 3. As seen from FIG. 3, Erbb1 78 exhibits excellent binding capacity to both antigens.

7. Measurement of Binding Capacity of Full-Length IgG

Figure 4:
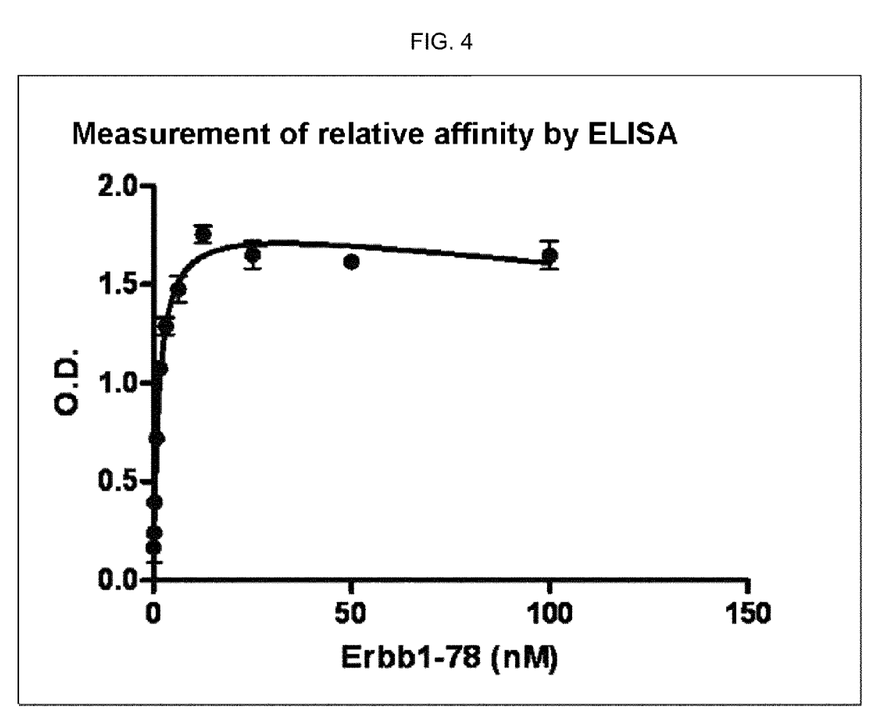
FIG. 4 is a graph showing the result of measuring binding capacity between a representative antibody Erbb1-78 and cells overexpressing epidermal growth factor receptor (EGFR) by enzyme-linked immunosorbent assay (ELISA).

Binding capacity between the antibody obtained in 5 and the A431 cell line (ATCC) which overexpresses EGFR is determined by ELISA [Biological efficacy of a chimeric antibody to the epidermal growth factor receptor in a human tumor xenograft model, *Clinic. Cancer res.*, 1995, vol. 1, 1311-1318] (the entire contents of which are incorporated herein by reference). The protocol for the ELISA assay is similar to that described in 6 above, except that antibody was used over a range of concentration and A431 cells were attached to the plate. As a result, Erbb1 78 is determined to exhibit a $K_d$ value of 1.088 nM at $B_{max}$=1.732 (see FIG. 4).

8. Measurement of Antibody Binding Capacity by Surface Plasmon Resonance (SPR)

More accurate measurements of the antibody binding capacity are made by SPR using a BIAcore (GE Healthcare, USA). Either 10 ug/mL Erbb1-Fc or EGFR_human is fixed on a sensor chip (CM5, GE Healthcare) using pH 4.5 acetate solution and an amine coupling kit (GE Healthcare). The Erbb1-78 antibody obtained in section 5 is diluted to 5 concentrations from 200 nM to 12.5 nM, and associated and dissociated (using pH 2.0 glycine solution) with the antigens fixed on the respective sensor chips for the measurement of antigen-antibody binding capacity. The results determined from analysis of the SPR data are given in Table 3.

TABLE 3

| Clone ID | On rate (1/Ms) | Off rate (1/s) | Affinity (Kd, nM) |
|---|---|---|---|
| Erbb1 78 | $6.17 \times 10^5$ | $2.991 \times 10^{-4}$ | 0.485 |

9. Measurement of Inhibition of EGF-EGFR Interaction by Antibody

A431 cells (ATCC) are treated with the full-length IgG obtained in section 5. After treating with EGF, change of phosphorylation ability of EGFR is measured using Phospho-Detect EGFR ELISA Kit (Calbiochem). Specifically, A431 cells are cultured on a 6-well culture plate (BD Falcon) up to 80% and then cultured for a day in serum-free DMEM (Invitrogen). The cell culture is treated with the antibody obtained in 5 at a concentration of 100 nM and the cells are then cultured for 2 hours. Subsequently, the cell culture is treated with EGF (Sigma) at a concentration of 1.7 nM for 15 minutes. The cells harvested from the culture medium and then lysed with 1 mM activated sodium vanadate (Sigma) and protease inhibitor cocktail (Roche). Then, ELISA is carried out on the lysed cells. The results are given in the following Table 4.

TABLE 4

| Antibody pretreatment | EGF treatment | Phosphorylation ability (%) |
|---|---|---|
| None | None | 65 |
| None | 1.7 nM, 15 min | 100 |
| Erbb1 78, 100 nM, 2 hr | 1.7 nM, 15 min | 70 |

Assuming that the phosphorylation ability of EGFR induced by EGF in the absence of interfering material is 100%, the basic phosphorylation ability in the absence of EGF is 65%. Following treatment with the antibody, the phosphorylation ability is 70% after EGF treatment. Thus the antibody inhibits over 80% of the phosphorylation activity of EGFR.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Description has been made in detail with reference to example embodiments. However, it will be appreciated by those skilled in the art that changes may be made in these embodiments without departing from the principles and spirit of the invention, the scope of which is defined in the accompanying claims and their equivalents.

What is claimed is:

1. An isolated human monoclonal antibody or a binding fragment thereof that binds human epidermal growth factor receptor (EGFR) wherein the antibody comprising a heavy chain variable domain comprising a heavy chain complementarity determining region (H-CDR) 1 (H-CDR1) sequence of SEQ ID NO: 1; an H-CDR2 sequence of SEQ ID NO: 2; and an H-CDR3 sequence of SEQ ID NO: 3; and a light chain variable domain comprising a light chain complementarity determining region (L-CDR) 1 (L-CDR1) sequence of SEQ ID NO: 4; an L-CDR2 sequence of SEQ ID NO: 5; and an L-CDR3 sequence of SEQ ID NO: 6; or a binding fragment thereof, wherein the fragment binds human EGFR.

2. An isolated epidermal growth factor receptor (EGFR)-specific fully human antibody or a binding fragment thereof wherein the antibody comprising a heavy chain encoded by a polynucleotide consisting of nucleotides 1-1401 of SEQ ID NO: 7; and a light chain encoded by a polynucleotide consisting of SEQ ID NO: 8, or a binding fragment thereof, wherein the fragment binds human EGFR.

3. A composition comprising the antibody or the binding fragment thereof of claim 1; and a pharmaceutically acceptable carrier.

4. A composition comprising a conjugated antibody or binding fragment thereof, wherein the antibody or the binding fragment thereof of claim 1 is linked to a toxic material, a chemotherapeutic agent, or a labeling material.

5. A method of detecting EGFR in a sample comprising
contacting the antibody or the binding fragment thereof of claim 1 with a sample under conditions such that the antibody binds EGFR; and
detecting antibody bound to EGFR.

6. A method of detecting EGFR in a sample comprising
contacting the antibody or the binding fragment thereof of claim 2 with a sample under conditions such that the antibody binds EGFR; and
detecting antibody or the binding fragment thereof bound to EGFR.

7. A composition comprising a conjugated antibody or binding fragment thereof, wherein the antibody or the binding fragment thereof of claim 2 is linked to a toxic material, a chemotherapeutic agent, or a labeling material.

8. A composition comprising the antibody or the binding fragment thereof of claim 2; and a pharmaceutically acceptable carrier.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Homo sapiens

<400> SEQUENCE: 1

Asp Tyr Gly Met Ser
 1               5

<210> SEQ ID NO 2
<211> LENGTH: 17
<212> TYPE: PRT
<213> ORGANISM: Homo sapiens

<400> SEQUENCE: 2

Gly Ile Asn Trp Asn Gly Gly Ser Thr Gly Tyr Ala Asp Ser Val Lys
 1               5                  10                  15

Gly

<210> SEQ ID NO 3
<211> LENGTH: 8
<212> TYPE: PRT
<213> ORGANISM: Homo sapiens

<400> SEQUENCE: 3

Asp Tyr Trp Gly Ser Leu Asp Tyr
 1               5

<210> SEQ ID NO 4
<211> LENGTH: 14
<212> TYPE: PRT
<213> ORGANISM: Homo sapiens

<400> SEQUENCE: 4
```

-continued

Thr Gly Thr Ser Ser Asp Val Gly Gly Tyr Asn Tyr Val Ser
 1               5                   10

<210> SEQ ID NO 5
<211> LENGTH: 7
<212> TYPE: PRT
<213> ORGANISM: Homo sapiens

<400> SEQUENCE: 5

Asp Val Asn Arg Arg Pro Ser
 1               5

<210> SEQ ID NO 6
<211> LENGTH: 10
<212> TYPE: PRT
<213> ORGANISM: Homo sapiens

<400> SEQUENCE: 6

Ser Ser Tyr Val Ser Thr Asn Thr Tyr Val
 1               5                   10

<210> SEQ ID NO 7
<211> LENGTH: 1419
<212> TYPE: DNA
<213> ORGANISM: Homo sapiens
<220> FEATURE:
<221> NAME/KEY: misc_feature
<222> LOCATION: (1)..(408)
<223> OTHER INFORMATION: CDR 1 to 3
<220> FEATURE:
<221> NAME/KEY: misc_feature
<222> LOCATION: (409)..(702)
<223> OTHER INFORMATION: CH 1
<220> FEATURE:
<221> NAME/KEY: misc_feature
<222> LOCATION: (703)..(738)
<223> OTHER INFORMATION: Hinge
<220> FEATURE:
<221> NAME/KEY: misc_feature
<222> LOCATION: (739)..(1077)
<223> OTHER INFORMATION: CH 2
<220> FEATURE:
<221> NAME/KEY: misc_feature
<222> LOCATION: (1078)..(1419)
<223> OTHER INFORMATION: CH 3
<220> FEATURE:
<221> NAME/KEY: misc_feature
<222> LOCATION: (1414)..(1419)
<223> OTHER INFORMATION: XhoI site

<400> SEQUENCE: 7
atgggatgga gctatatcat cctcttttg gtggccacag cggccgatgt ccactcgcag      60
atgcagctgg tgcagtctgg gggaggtgtg gtacggcctg gggggtccct gagactctcc    120
tgtgcagcct ctggattcac ctttgatgat tatggcatga gctgggtccg ccaagctcca    180
gggaaggggc tggagtgggt tctctggtatt aattggaatg gtggtagcac aggttatgca   240
gactctgtga agggccgatt caccatctcc agagacaacg ccaagaactc cctgtatctg    300
caaatgaaca gtctgagagc cgaggacacg gccgtgtatt actgtgcgag agactactgg    360
ggatcgcttg actactgggg ccagggaacc ctgatcaccg tctcctcagc tagcaccaag    420
ggcccatcgg tcttccccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcctgggca cccagaccta catctgcaac    660
gtgaatcaca agcccagcaa caccaaggtg gacaagaaag ttgagcccaa atcttgtgac    720

```
aaaactcaca catgcccacc gtgcccagca cctgaactcc tggggggacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc      1020
aaggtctcca acaaagccct cccagccccc atcgagaaaa ccatctccaa agccaaaggg      1080
cagccccgag aaccacaggt gtacaccctg cccccatccc gggaggagat gaccaagaac      1140
caggtcagcc tgacctgcct ggtcaaaggc ttctatccca gcgacatcgc cgtggagtgg      1200
gagagcaatg ggcagccgga gaacaactac aagaccacgc ctcccgtgct ggactccgac      1260
ggctccttct tcctctacag caagctcacc gtggacaaga gcaggtggca gcaggggaac      1320
gtcttctcat gctccgtgat gcatgaggct ctgcacaacc actacacgca gaagagcctc      1380
tccctgtctc cgggtaaatg agtgcgacgg ccgctcgag                             1419

<210> SEQ ID NO 8
<211> LENGTH: 666
<212> TYPE: DNA
<213> ORGANISM: Homo sapiens
<220> FEATURE:
<221> NAME/KEY: misc_feature
<222> LOCATION: (1)..(382)
<223> OTHER INFORMATION: CDR 1 to 3
<220> FEATURE:
<221> NAME/KEY: misc_feature
<222> LOCATION: (383)..(666)
<223> OTHER INFORMATION: CL

<400> SEQUENCE: 8
atgggatgga gctatatcat cctcttttg gtggccacag cggccgatgt ccactcgcag      60
tctgccctga ctcagcctgc ctccgtgtct gggtctcctg gacagtcgat caccatctcc      120
tgcactggaa ccagcagtga cgttggtggc tataactatg tctcctggta ccaacagaac      180
tcaggcaaag cccccaaact catgattcat gatgtcaata gcggcccctc aggggtttct      240
aatcgcttct ctggctccaa gtctggcaac acggcctccc tgaccatcgc tgggctccag      300
gctgacgacg aggctgatta ttactgcagc tcatatgtaa gcaccaacac ttatgtcttc      360
ggaactggga ccaaggtcac cgtcctaaga tctgtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaac acaaagtcta cgcctgcgag tcacccatca      660
ggctga                                                                 666
```